(12) United States Patent
Arai et al.

(10) Patent No.: US 7,323,144 B2
(45) Date of Patent: Jan. 29, 2008

(54) APPARATUS FOR SEPARATING BIOLOGICAL SAMPLE AND SEPARATING METHOD OF THE SAME

(75) Inventors: Kousuke Arai, Nerima-Ku (JP); Noriyuki Nomura, Kawaguchi (JP)

(73) Assignee: Leisure, Inc., Tokyo (JP)

( * ) Notice: Subject to any disclaimer, the term of this patent is extended or adjusted under 35 U.S.C. 154(b) by 577 days.

(21) Appl. No.: 10/382,901

(22) Filed: Mar. 7, 2003

(65) Prior Publication Data

US 2003/0175167 A1 Sep. 18, 2003

(30) Foreign Application Priority Data

Mar. 18, 2002 (JP) ............................. 2002-074616

(51) Int. Cl.
*B01L 11/00* (2006.01)

(52) U.S. Cl. ..................... 422/101; 422/61; 422/68.1; 422/102; 436/69; 436/174; 436/175; 436/177

(58) Field of Classification Search .......... 422/99–102, 422/61, 68.1; 436/69, 70, 174, 176, 177, 436/178; 210/136, 634, 644, 645, 646, 649

See application file for complete search history.

(56) References Cited

U.S. PATENT DOCUMENTS

| | | | | |
|---|---|---|---|---|
| 3,586,064 A | * | 6/1971 | Brown et al. .................... | 141/1 |
| 3,799,342 A | * | 3/1974 | Greenspan .................... | 210/780 |
| 3,814,258 A | | 6/1974 | Ayres | |
| 3,846,077 A | * | 11/1974 | Ohringer ..................... | 422/100 |
| 3,849,072 A | * | 11/1974 | Ayres .......................... | 210/789 |
| 3,932,277 A | | 1/1976 | McDermott et al. | |
| 3,954,614 A | | 5/1976 | Wright | |
| 4,057,499 A | | 11/1977 | Buono | |
| 4,189,385 A | * | 2/1980 | Greenspan ................... | 210/136 |
| 4,210,623 A | | 7/1980 | Breno et al. | |
| 5,110,558 A | * | 5/1992 | Romer ....................... | 422/101 |
| 5,376,337 A | * | 12/1994 | Seymour .................... | 422/101 |
| 6,063,038 A | * | 5/2000 | Diamond et al. ........... | 600/569 |

\* cited by examiner

*Primary Examiner*—Jill Warden
*Assistant Examiner*—Dwayne K Handy
(74) *Attorney, Agent, or Firm*—Jacobson Holman PLLC

(57) ABSTRACT

A simplified collecting operation of a biological sample is provided, which enables reduction of the examination cost. The invention comprises a biological sample collecting means 2 for receiving a collected biological sample, a filtering means 21 for passing a predetermined component within the collected biological sample therethrough, a separated component containing means 3 capable of being fitted into the biological sample collecting means 2, for receiving the predetermined component that is passed through the filtering means 21, and a reverse-flow preventing means 5 for preventing the predetermined component received in the separated component containing means 3 from flowing backward into the biological sample collecting means 2 through the filtering means 21, wherein once the biological sample is collected in the biological sample collecting means 2 and the separated component containing means 3 is fitted into the biological sample collecting means 2, and after the predetermined component within the biological sample is passed through the filtering means 21, then the reverse-flow preventing means 5 closes a flow path between the separated component containing means 3 and the biological sample collecting means 2 to prevent a reverse flow of the predetermined component, and the predetermined component of the biological sample is separately received in the separated component containing means 3.

8 Claims, 8 Drawing Sheets

FIG. 2
FIG. 3
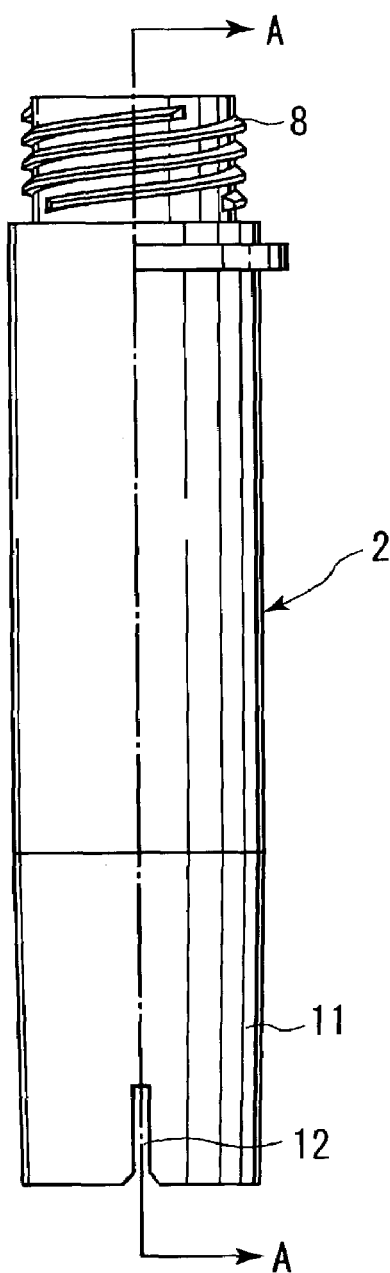
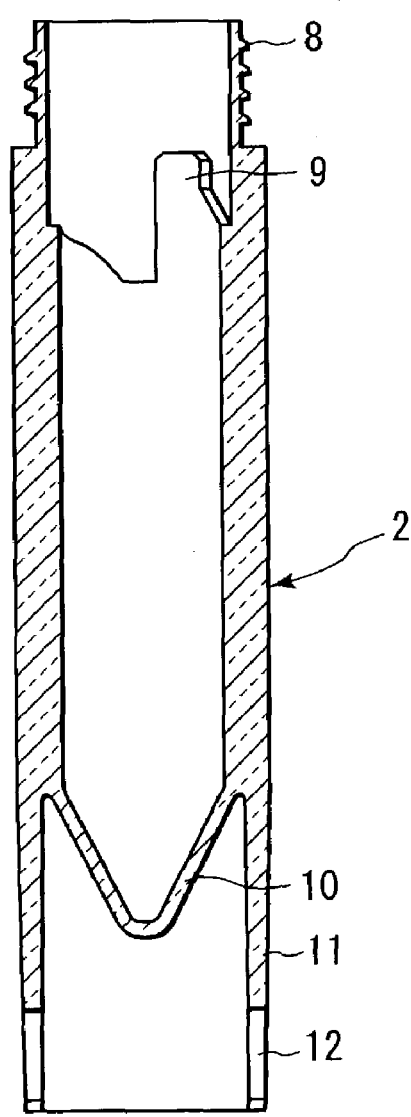

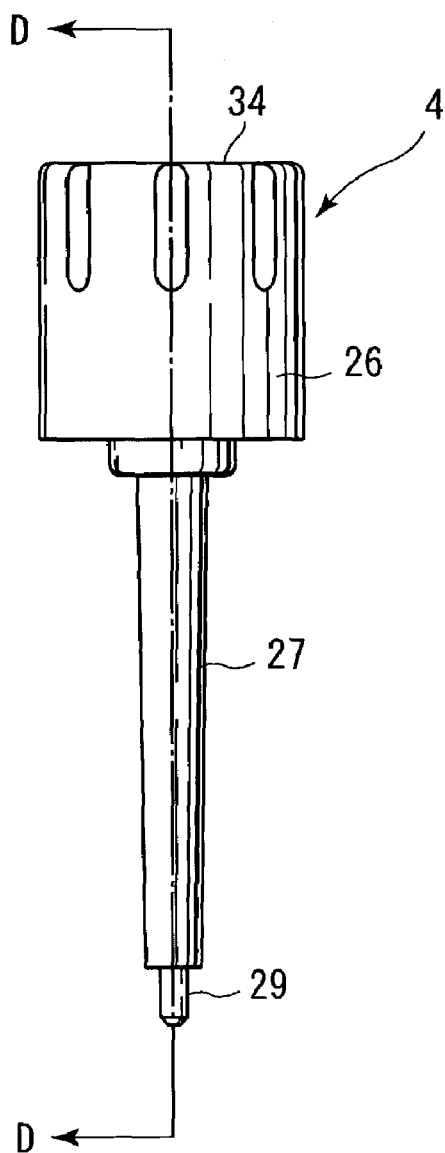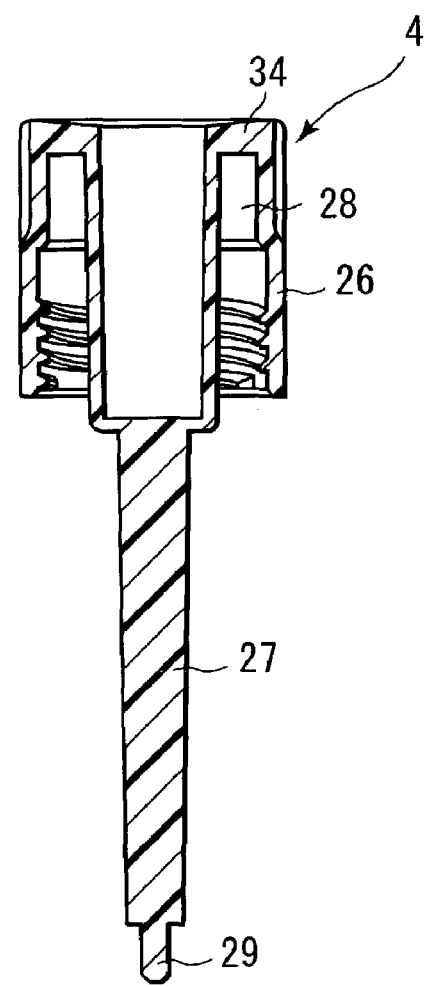

APPARATUS FOR SEPARATING BIOLOGICAL SAMPLE AND SEPARATING METHOD OF THE SAME

FIELD OF THE INVENTION

The present invention relates to an apparatus for separating a biological sample and a separating method of the same, specifically to a blood-separating apparatus for separating collected blood into blood cells and plasmas or serums, and the separating method of the collected blood.

BACKGROUND OF THE INVENTION

Generally in conventional laboratory examination, a person having a certain license or a specialized technician such as a doctor, a nurse, or a clinical laboratory technician collects a biological sample by means of for example blood sample collection, and then performs a predetermined test based on the collected biological sample.

In manner of conventional biochemical examination however, it has been necessary for a subject to visit a hospital or a center for clinical examination where the licensed person or the specialized technician such as a doctor, a nurse, a clinical laboratory technician or the like is available, or conversely, such a licensed person or specialized technician may have to visit a place where the subject is located, in order to collect the biological sample. Thus, collecting biological samples has been very troublesome and caused an increase in the examination cost.

Further, since raw blood changes quickly with time, fluctuation in accuracy of the examination has occurred. Accordingly, there has been a need to develop an examination apparatus capable of producing more accurate test result by separating the blood immediately after the blood sample is collected.

In addition, although a method of collecting the biological sample by the subject by himself has been practiced in order to simplify the operation of collecting the biological sample, this method has been problematic in that it is only effective in some examination items and not applicable to other examination items.

The present invention has been carried out in the light of the above-described conditions and it provides the apparatus for separating the biological sample and the separating method of the same, which are capable of simplifying the collecting operation of the biological sample, improving the accuracy of the examination, and lowering the examination cost.

SUMMARY OF THE INVENTION

The present invention comprises a biological sample collecting container for receiving a collected biological sample, a filter for passing a predetermined component within the collected biological sample therethrough, a separated component container capable of being fitted into the biological sample collecting container, for receiving the predetermined component that is passed through the filter, and a reverse-flow preventing member for preventing the predetermined component received in the separated component container from flowing backward into the biological sample collecting container through the filter, wherein once the biological sample is collected in the biological sample collecting container and the separated component container is fitted into the biological sample collecting container, and after the predetermined component within the biological sample is passed through the filter, the reverse-flow preventing member closes a flow path between the separated component container and the biological sample collecting container to prevent a reverse flow of the predetermined component, and the predetermined component of the biological sample is separately received in the separated component container.

Preferably, the present invention comprises a blood-collecting container for receiving collected blood, a filtration film for allowing plasmas or serums within the collected blood to pass through while blocking the passage of blood cells, a cylindrical body capable of being fitted into the blood-collecting container and of receiving the plasmas or serums that are passed through the filtration film, and a sealing cap for preventing the plasmas or serums received in the cylindrical body from flowing backward into the blood-collecting container through the filtration film, wherein once the blood is collected in the blood-collecting container and the cylindrical body is fitted into the blood-collecting container, and after the plasmas or serums within the blood are passed through the filtration film, then the sealing cap closes a flow path between the cylindrical body and the blood-collecting container to prevent a reverse flow of the plasmas or serums, and the blood cells and the plasmas or serums are separately received in the blood-collecting container and the cylindrical body respectively.

More preferably, a diluent solution is placed within the blood-collecting container.

Further, the present invention is characterized in that the blood-collecting container has the same outer diameter as a sample cup of a biochemical analyzer and has a screw part provided at an upper end part thereof, the filtration film is provided at a lower end part of the cylindrical body, the cylindrical body has a cap piston crowned thereon, the cap piston is provided with a grip part that can be threaded into the screw part and a stem part extending from the grip part into the cylindrical body, and the sealing cap is provided at a lower end of the stem part, and in that once the blood is collected in the blood-collecting container and the cylindrical body is fitted into the blood-collecting container followed by threading the grip part into the screw part, and after the plasmas or serums within the blood are passed through the filtration film, then the sealing cap closes the lower end part of the cylindrical body to prevent the reverse flow of the plasmas or serums, and the plasmas or serums and the blood cells are separately received in the cylindrical body and the blood-collecting container respectively.

Furthermore, the present invention is characterized in that the cylindrical body has an upper end part into which the cap piston can be fitted, and a main body part that can be separated from the upper end part and locked to the blood-collecting container, and in that once the grip part is threaded into the screw part of the blood-collecting container, the main body part is locked to the blood-collecting container to restrain the movement of the main body part and to separate the upper end part from the main body part.

Further, the present invention is characterized in that the sealing cap is provided at a lower end of the stem part and at a lower end part of the cylindrical body such that the sealing cap can be detached from the lower end of the stem part and fitted into the lower end part of the cylindrical body respectively, and once the mated condition between the grip part and the screw part of the blood-collecting container is released and the cap piston is pulled out, the sealing cap is broken off from the lower end of the stem part to maintain the sealed condition of the lower end part of the cylindrical body.

The present invention comprises the steps of fitting a separated component container into a biological sample collecting container that has the biological sample collected, and receiving a predetermined component within the biological sample into the separated component container through a filter, and after receiving the predetermined component into the separated component container, the steps of closing a flow path between the separated component container and the biological sample collecting container by a reverse-flow preventing member, preventing the reverse flow of the predetermined component, and separately receiving the predetermined component into the separated component container.

Further, the present invention comprises the steps of fitting a cylindrical body into a blood-collecting container that has the blood collected, threading a grip part of a cap piston crowned on the cylindrical body into a screw part of the blood-collecting container, and receiving plasmas or serums within the blood into the cylindrical body through a filtration film, and after receiving the plasmas or serums into the cylindrical body, the steps of closing a flow path between the cylindrical body and the blood-collecting container by a sealing cap, preventing a reverse flow of the plasmas or serums, and separately receiving the plasmas or serums into the cylindrical body and blood cells into the blood-collecting container respectively.

According to the present invention described above, a simplified collecting operation of the biological sample is provided, which enables reduction of the examination cost. Also, since the biological sample can be completely separated, the temporal change of a specimen can be prevented to make the examination highly accurate.

BRIEF DESCRIPTION OF THE DRAWINGS

FIG. 2 is a side elevation view of a blood-collecting container according to the embodiment of the present invention;

FIG. 3 is the cross sectional view of FIG. 2 taken along the line A-A;

FIG. 8 is the side elevation view of a cap piston according to the embodiment of the present invention;

FIG. 9 is the cross sectional view of FIG. 8 taken along the line D-D;

DESCRIPTION OF THE PREFERRED EMBODIMENT

Figure 1:
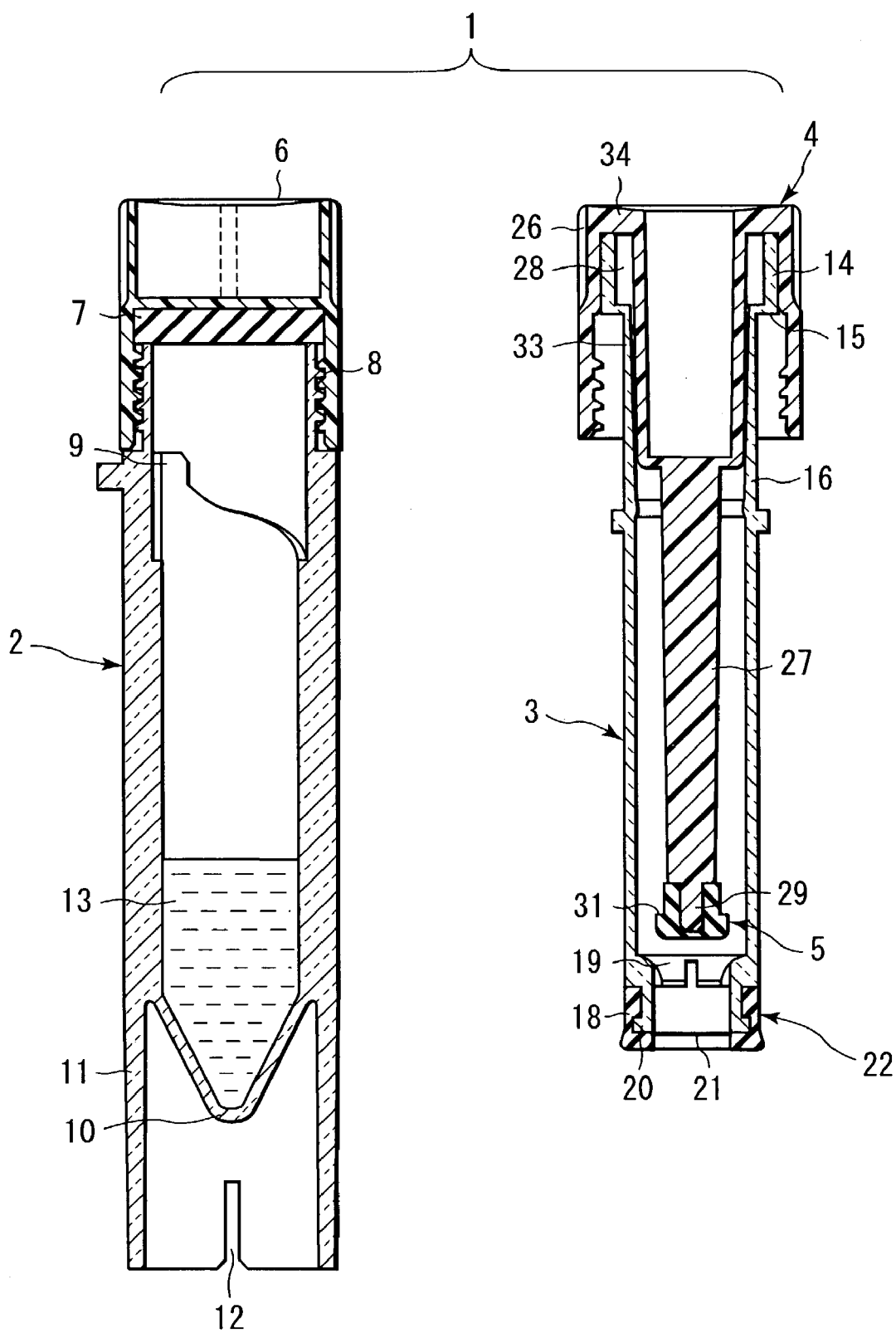
FIG. 1 is a cross sectional view of a blood-separating apparatus according to an embodiment of the present invention.

A biological sample separating apparatus and its separating method according to an embodiment of the present invention will now be described in detail with reference to the drawings.

FIGS. 1-13 illustrate a case of using blood as a biological sample. A blood-separating apparatus 1 in this case comprises a blood-collecting container 2, a cylindrical body 3 capable of being fitted into the blood-collecting container 2, a cap piston 4 capable of being crowned on the cylinder body 3, and a sealing cap 5 provided at the lower end of the cap piston 4, wherein the upper end opening of the blood-collecting container 2 is sealed by a cap 6 via a packing 7 before use as shown in FIG. 1.

As best shown in FIG. 2 and FIG. 3, the blood-collecting container 2 is made of transparent material and of a cylindrical shape, wherein the upper end part of the blood-collecting container 2 has a screw part 8 on the outer surface thereof and a locking part 9 protrudingly formed on the inner surface thereof. Also, at the lower end part of the blood-collecting container 2 is formed a bottom 10 of the shape of an inverted cone and around the bottom 10 is formed a leg 11 of the shape of a cylinder. The leg 11 has the same outer diameter as a sample cup to be used in blood analysis and examination, and preferably has slits 12 formed vertically in the lower end of the leg at opposing positions respectively. Further, a predetermined amount of diluent solution 13, for example 500 $mm^3$, is placed beforehand within the blood-collecting container 2 as shown in FIG. 1.

Figure 4:
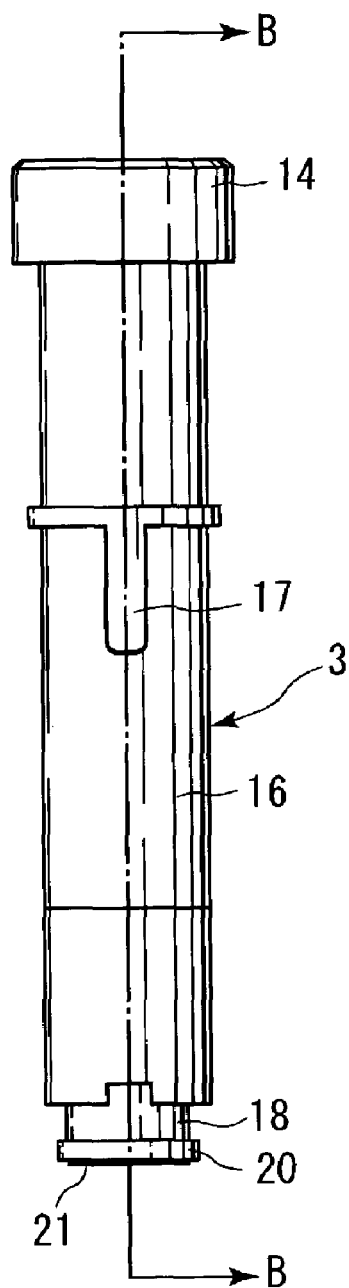
FIG. 4 is the side elevation view of a cylindrical body according to the embodiment of the present invention.
Figure 5:
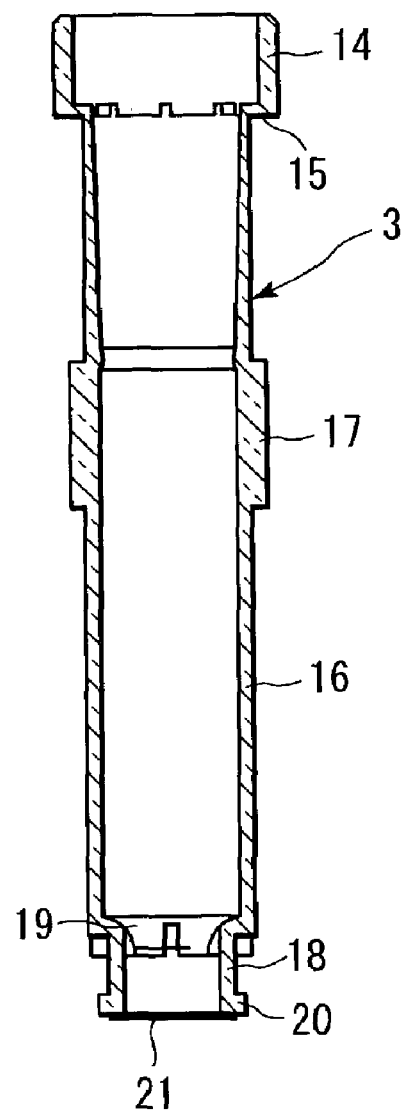
FIG. 5 is the cross sectional view of FIG. 4 taken along the line B-B.

As best shown in FIG. 4 and FIG. 5, the cylinder body 3 is made of the transparent material and of the cylindrical shape, wherein a diameter-extended part 14 is formed at the upper end part thereof. The diameter-extended part 14 is connected to a main body part 16 through a thin walled part 15, and stopper parts 17 are protrudingly formed vertically in the middle portion of the main body part 16. Also, a diameter-contracted part 18 is formed at the lower end part of the cylinder body 3, and the inner surface of the diameter-contracted part 18 is formed a protruded locking part 19. Further, the diameter-contracted part 18 has an outer flange 20 formed at the lower part thereof, and a lower end opening of the outer flange 20 is covered with a filtration film 21, which is adapted to allow plasmas or serums within the blood to pass through it, but block blood cells.

Figure 6:
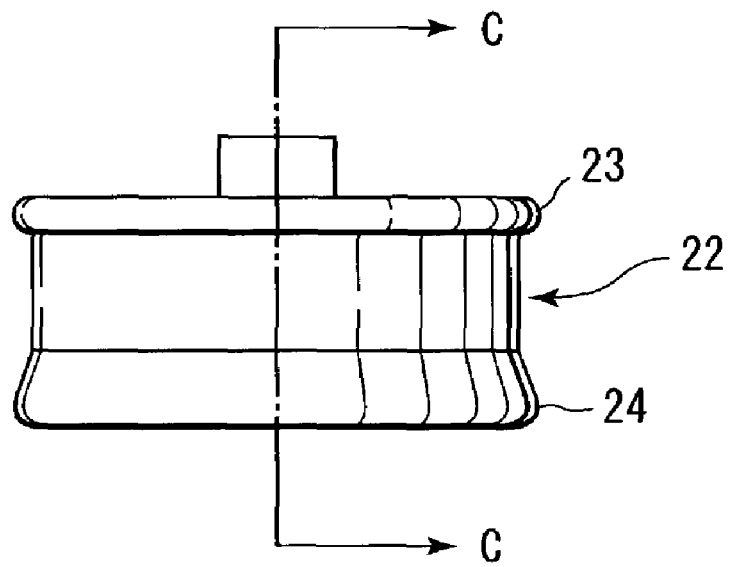
FIG. 6 is the side elevation view of a cover according to the embodiment of the present invention.
Figure 7:
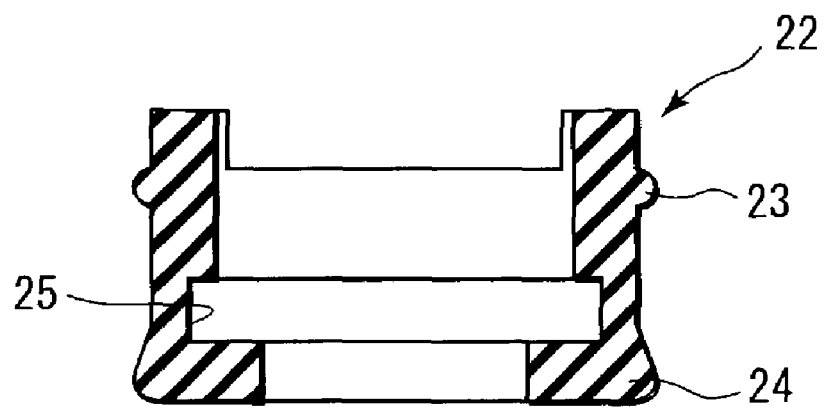
FIG. 7 is the cross sectional view of FIG. 6 taken along the line C-C.

A cover 22, which is made of silicon rubber, is attached to the outer periphery of the diameter-contracted part 18 (see FIG. 1). As best shown in FIG. 6 and FIG. 7, the cover 22 has a protruded part 23 formed on the outer periphery of the upper end part thereof and the lower end part 24 thereof has a gradually increasing diameter toward the end, so that the outer diameters of the protruded part 23 and the lower end part 24 are slightly larger than the outer diameter of the main body part 16. Further, the cover 22 has a peripheral groove 25 formed in the inner surface thereof, and the outer flange 20 is fitted into the peripheral groove 25 so as to prevent the cover 22 from slipping off from the diameter-contracted part 18.

Figure 10:
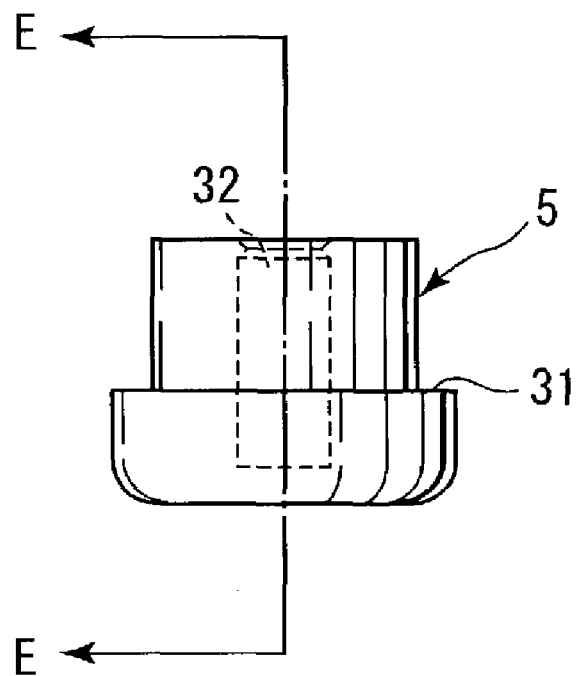
FIG. 10 is the side elevation view of a sealing cap according to the present invention.
Figure 11:
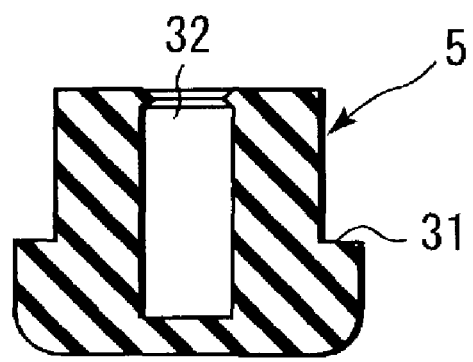
FIG. 11 is the cross sectional view of FIG. 10 taken along the line E-E.

The cap piston 4, as best shown in FIG. 8 and FIG. 9, is comprised of a generally cylindrical grip part 26, and a stem part 27 extending downward concentrically with the grip part 26. The grip part 26 has a cylindrical space 28 formed in the inner upper end part thereof, into which the diameter-extended part 14 of the cylindrical body 3 can be fitted, and threads are formed in the part below the space so that the screw part 8 can be threaded into that part. The stem part 27 has a lower end 29 formed into a pin shape, to which the sealing cap 5 is detachably attached (see FIG. 1). The sealing cap 5 is made of the silicon rubber and has a generally cylindrical form with a lower part formed into an outer flange, thus creating a step part 31 on the outer periphery of the lower part of the sealing cap, as best shown in FIG. 10 and FIG. 11. Further, in the sealing cap 5 is formed a groove 32 into which the lower end 29 of the stem part 27 can be detachably fitted.

Figure 12:
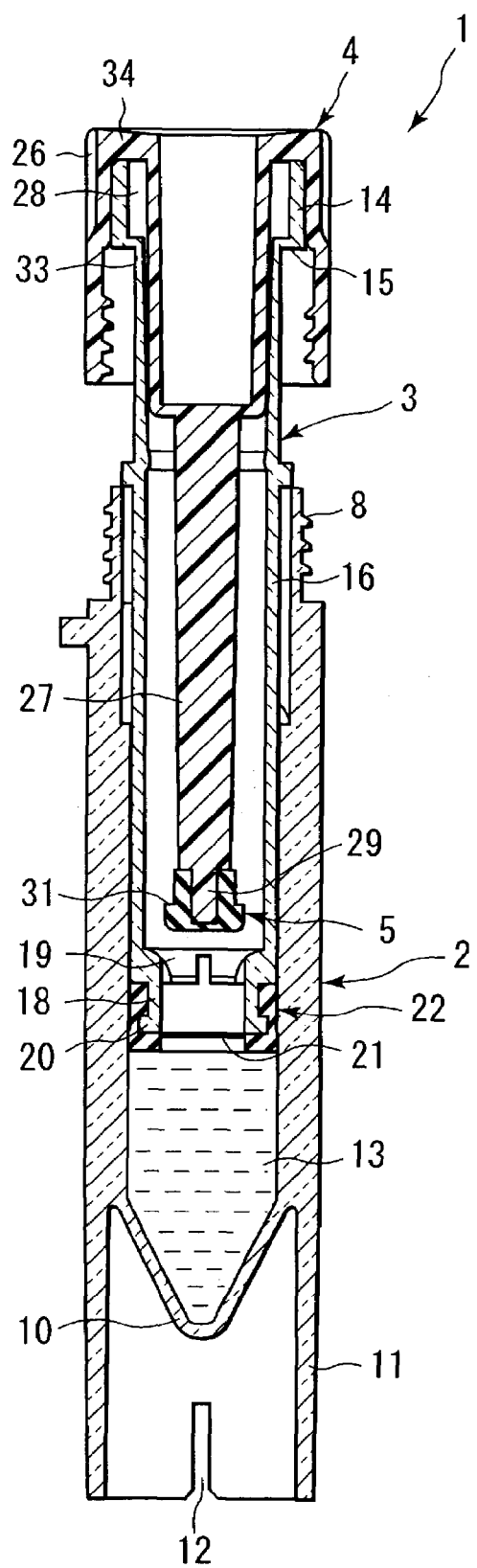
FIG. 12 is the cross sectional view illustrating the operation of the blood-separating apparatus according to the embodiment of the present invention.
Figure 13:
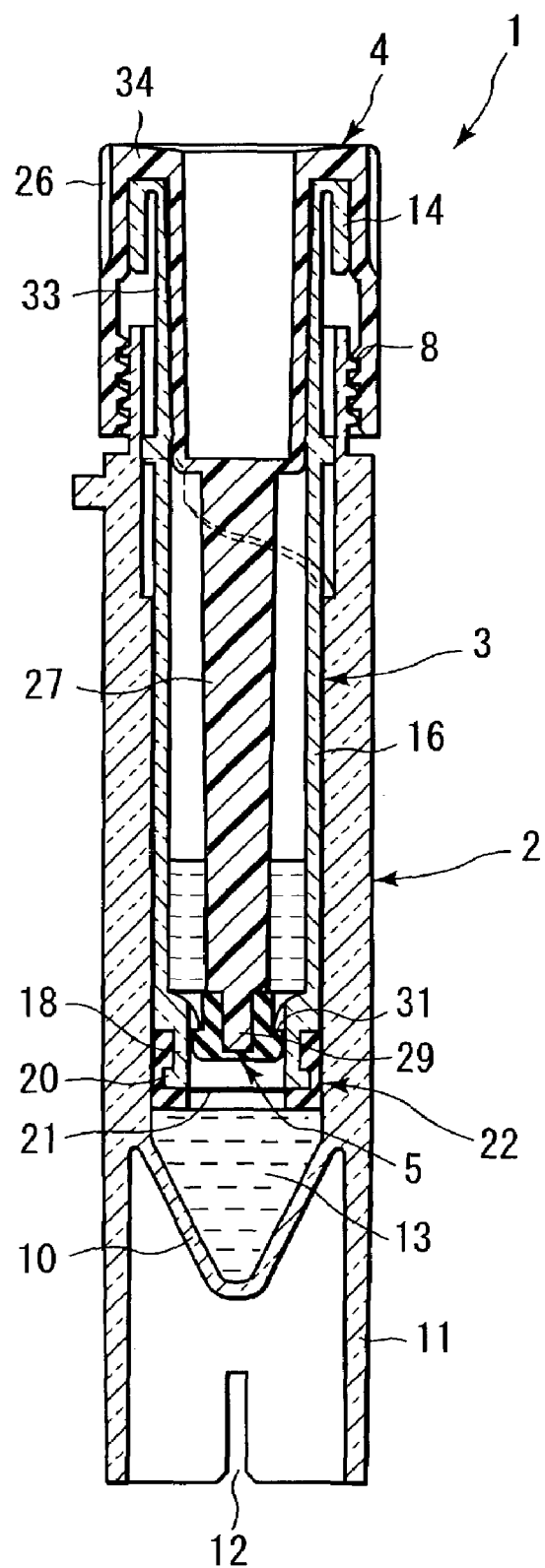
FIG. 13 is the cross sectional view illustrating the operation of the blood-separating apparatus according to the embodiment of the present invention.

The method of separating the blood according to the embodiment of the present invention will be now described with reference to FIG. 1 and FIGS. 12-13.

After removing the cap 6 and the packing 7 from the blood-collecting container 2, the subject stings a blood-collecting needle on his finger or the like to collect a small amount, for example 1-2 drops of blood into the blood-collecting container 2. The collected blood is gradually separated into blood cells and plasmas or serums within the diluent solution 13, and the blood cells begin to clot and deposit in the diluent solution 13 while the plasmas or serums begin to float within the diluent solution 13. In this condition, the cylindrical body 3 with the cap piston 4 crowned thereon is fitted into the blood-collecting container 2 while the screw part 8 is threaded into the grip part 26 as shown in FIG. 12. At first, the cylindrical body 3 rotates with the grip part 26, but once the locking part 9 is locked on the stopper part 17, the rotation of the cylindrical body 3 is restrained and the thin walled part 15 is twisted to rupture, resulting in separation of the cylindrical body 3 into the main body part 16 and the diameter-extended part 14. Then, when the grip part 26 is further rotated, the upper end part 33 of the main body part 16 intrudes the space 28 into the inside of the diameter-extended part 14 and becomes to be pressed downward by the inner surface of a top 34 of the grip part 26, thus lowering the cylindrical body 3 further. As the cylindrical body 3 is lowered, the plasmas or serums suspended within the diluent solution 13 pass through the filtration film 21 to move into the cylindrical body 3, while the blood cells cannot pass through the filtration film 21 and remain within the blood-collecting container 2. At this point of time, since the outer diameters of the protruded part 23 and the lower end part 24 of the cover 22 are greater than the outer diameter of the main body part 16 of the cylindrical body 3, the cylindrical body 3 is lowered with the inner surface of the blood-collecting container 2 being closely contacted therewith. Accordingly, during the process of fitting the cylindrical body 3 into the blood-collecting container 2, there is no possibility of leaking the blood or the diluent solution 13 from the blood-collecting container 2 to the outside thereof through a gap between the blood-collecting container 2 and the cylindrical body 3. Then, when the grip part 26 is threaded into the screw part 8 to its lowest part, the sealing cap 5 is mated with the diameter-contracted part 18 to seal the flow path between the blood-collecting container 2 and the cylindrical body 3, thereby maintaining assuredly the separated condition between the blood cells and the plasmas or serums.

The blood-separating apparatus 1 is then transported with keeping this condition to an examination site where the grip part 26 is detached by rotating it. At this moment, the step part 31 of the sealing cap 5 is locked on the protruded locking part 19 and the sealing cap 5 is separated from the lower end 29 of the stem part 27 to remain within the diameter-contracted part 18, so that only the grip part 26 and the stem part 27 are removed thereby creating no possibility of mixing the blood cells with the plasmas or serums. After that, the cylindrical body 3 is taken out from the blood-collecting container 2, and the blood cells in the blood-collecting container 2 and the plasmas or serums in the cylindrical body 3 respectively are analyzed using analytical instruments to conduct a predetermined examination. At this moment, since the blood-collecting container 2 has the same outer diameter as that of the sample cup, the blood-collecting container 2 can be placed directly in the analytical instrument without transferring the blood cells from the blood-collecting container into the sample cup, which provides for improvement in the operating efficiency and minimization of the amount of the blood to collect.

As such, the present invention can separate the blood into the blood cells and the plasmas or serums in situ immediately after the blood has been collected and transport it to the examination site with keeping the separated condition unchanged, which therefore prevents hemolysis, clotting and the like of the blood during transportation. Accordingly, the blood will be well preserved and improvement of the examination accuracy can be provided. In addition, since the blood separation does not use a centrifugal separator, only a minute amount of the collected blood may be required, and yet all the same examination items to those necessary for the usual examination can be conducted.

It is noted that, although in the above embodiment the cap piston 4 is adapted to be screwed into the blood collection container 2, the connection method is not limited to the use of threaded component and may include other methods such as forming a taper, as long as they provide a detachable connection capable of keeping its air-tightness.

Further, although in the above embodiment the implementation of the invention for the case of self blood-collection has been described where the subject collects his blood by himself, it will be obvious that the present invention can be implemented for a general blood collection where a licensed person such as a doctor collects the blood by using an injection syringe.

Furthermore, although in the above embodiment the case of using the blood as a biological sample has been described, the present invention can be implemented for the biological samples other than the blood, such as urine, feces, pleural effusion, ascites, saliva, and the like.

According to the present invention as described above, a simplified collecting operation of the biological samples is provided, which enables reduction of the examination cost. Furthermore, since the biological sample can be completely separated, various superior effects may be demonstrated, including for example that the temporal change of a specimen can be prevented to make the examination highly accurate.

What is claimed is:

1. An apparatus for separating a biological sample, comprising:
   a blood-collecting container for receiving collected blood;
   a diluent solution in an amount sufficient to dilute 1-2 drops of collected blood contained in said blood-collecting container;
   a filtration film through which plasmas or serums within the collected blood can pass while the passage of blood cells are blocked;
   a cylindrical body fittable into said blood-collecting container and capable of receiving the plasmas or serums that are passed through said filtration film; and
   a sealing cap for closing a flow path between said cylindrical body and said blood-collecting container for preventing the plasmas or serums received in the cylindrical body from flowing backward into said blood-collecting container through said filtration film once the blood is collected in said blood-collecting container and said cylindrical body is fitted into said blood-collecting container, and after the plasmas or serums within said blood are passed through said filtration film, whereby the blood cells and the plasmas or serums are separately received in said blood-collecting container and said cylindrical body respectively, wherein said blood-collecting container has a screw part provided at an upper end part of said container, said filtration film is provided at a lower end part of said cylindrical body, said cylindrical body has a cap piston crowned thereon, said cap piston is provided with a grip part that can be threaded into said screw part and a stem part extending from said grip part into said cylindrical body, and said sealing cap is provided at a lower end of said stem part; and wherein once the blood is collected in said blood-collecting container and said cylindrical body is fitted into said blood-collecting container followed by threading said grip part into said screw part, and after the plasmas or serums within said blood are passed through said filtration film, then said sealing cap closes the lower end part of said cylindrical body to prevent the reverse flow of said plasmas or serums, and the plasmas or serums and the blood cells are separately received in said cylindrical body and said blood-collecting container respectively.

2. The apparatus for separating a biological sample according to claim 1, wherein said cylindrical body has an upper end part into which said cap piston can be fitted, and a main body part that can be separated from said upper end part and locked to said blood-collecting container; and wherein once said grip part is threaded into the screw part of said blood-collecting container, said main body part is locked to said blood-collecting container to restrain the movement of said main body part and to separate said upper end part from said main body part.

3. The apparatus for separating for a biological sample according to claim 2, wherein said sealing cap is provided at a lower end of said stem part and at a lower end part of said cylindrical body such that said sealing cap can be detached from said lower end of said stem part and fitted into said lower end part of said cylindrical body respectively, and once the mated condition between said grip part and the screw part of said blood-collecting container is released and said cap piston is pulled out, said sealing cap is broken off from the lower end of said stem part to maintain the sealed condition of the lower end part of said cylindrical body.

4. The apparatus for separating a biological sample according to claim 1, wherein said blood-collecting container has the same outer diameter as a sample cup of a biochemical analyzer.

5. An apparatus for separating a biological sample, comprising:

biological sample collecting means for receiving a collected biological sample;

a diluent solution in an amount sufficient to dilute the collected biological sample contained in said biological sample collecting means;

filtering means for passing a predetermined component within said collected biological sample therethrough;

separated component containing means fittable into said biological sample collecting means, for receiving said predetermined component that is passed through said filtering means; and reverse-flow preventing means for closing a flow path between said separated component containing means and said biological sample collecting means for preventing said predetermined component received in said separated component containing means from flowing backward into said biological sample collecting means through said filtering means wherein once the biological sample is collected in said biological sample collecting means and said separated component containing means is fitted into said biological sample collecting means, and after the predetermined component within said biological sample is passed through said filtering means, whereby the predetermined component of said biological sample is separately received in said separated component containing means, wherein:

said biological sample collecting means is a container having a screw part provided at an upper end part thereof;

said separated component containing means has a cylindrical body having a cap piston crowned thereon, said cap piston being provided with a grip part threadable into said screw part and a stem part extending from said grip part into said cylindrical body, said filtering means is provided at a lower end part of said cylindrical body, and said reverse-flow preventing means is provided at a lower end of said stem part; and wherein once the biological sample is collected in said container and said cylindrical body is fitted into said container followed by threading said grip part into said screw part, and after the predetermined component within said biological sample is passed through said filtering means, then said reverse-flow preventing means closes the lower end part of said cylindrical body to prevent the reverse flow of said predetermined component, and the predetermined component is separately received in said separated component containing means.

6. The apparatus for separating a biological sample according to claim 5, wherein said cylindrical body has an upper end part into which said cap piston can be fitted, and a main body part that can be separated from said upper end part and locked to said container; and wherein once said grip part is threaded into the screw part of said container, said main body part is locked to said container to restrain the movement of said main body part and to separate said upper end part from said main body part.

7. The apparatus for separating for a biological sample according to claim 6, wherein said reverse-flow preventing means is provided at a lower end of said stem part and at a lower end part of said cylindrical body and includes means for detaching said reverse-flow preventing means from said lower end of said stem part and fitting said reverse-flow preventing means into said lower end part of said cylindrical body respectively, and for breaking off said reverse-flow preventing means from the lower end of said stem part to maintain the sealed condition of the lower end part of said cylindrical body once the mated condition between said grip part and the screw part of said container is released and said cap piston is pulled out.

8. The apparatus for separating a biological sample according to claim 5, wherein said biological sample collecting means has the same outer diameter as a sample cup of a biochemical analyzer.

* * * * *